United States Patent [19]

Nelson et al.

[11] Patent Number: 4,494,652
[45] Date of Patent: Jan. 22, 1985

[54] CONTAINER FOR SHARPS

[75] Inventors: Ralph E. Nelson; Ann L. Nelson; Evelyn J. Bogner; Paul M. Bogner, all of Newport Beach, Calif.

[73] Assignee: Winfield Industries, San Diego, Calif.

[21] Appl. No.: 510,050

[22] Filed: Jul. 1, 1983

[51] Int. Cl.³ .................. A61M 5/32; B02C 19/12; B65F 7/00; B26F 3/00
[52] U.S. Cl. ................... 206/366; 206/63.5; 206/370; 206/380
[58] Field of Search .............. 206/366, 365, 370, 380, 206/381, 63.5, 216; 225/93; 241/99

[56] References Cited

U.S. PATENT DOCUMENTS

| 357,421 | 2/1887 | Spencer | 206/63.5 |
| 3,469,750 | 9/1969 | Vanderbeck | 241/99 |
| 3,683,733 | 8/1972 | Johan et al. | 241/99 |
| 3,796,359 | 3/1974 | Dick | 206/365 |
| 4,351,434 | 9/1982 | Elisha | 206/366 |
| 4,375,849 | 3/1983 | Hanifl | 206/366 |
| 4,452,358 | 6/1984 | Simpson | 206/366 |
| 4,454,944 | 6/1984 | Shillington | 206/366 |

Primary Examiner—William T. Dixson, Jr.
Attorney, Agent, or Firm—Ellsworth R. Roston; Charles H. Schwartz

[57] ABSTRACT

A system for disposal of dangerous sharp articles and dangerous liquids, particularly those which represent the waste in certain medical procedures, includes an inner container and closure means and an outer wide mouthed, necked container whose receiving opening is closed against removal of material by a tapered, preferably conical insert which is divided into flaps and alternative covers, one to facilitate separation of syringe needles and thin barrels and the other to lock the outer container closed.

35 Claims, 6 Drawing Figures

U.S. Patent  Jan. 22, 1985  4,494,652
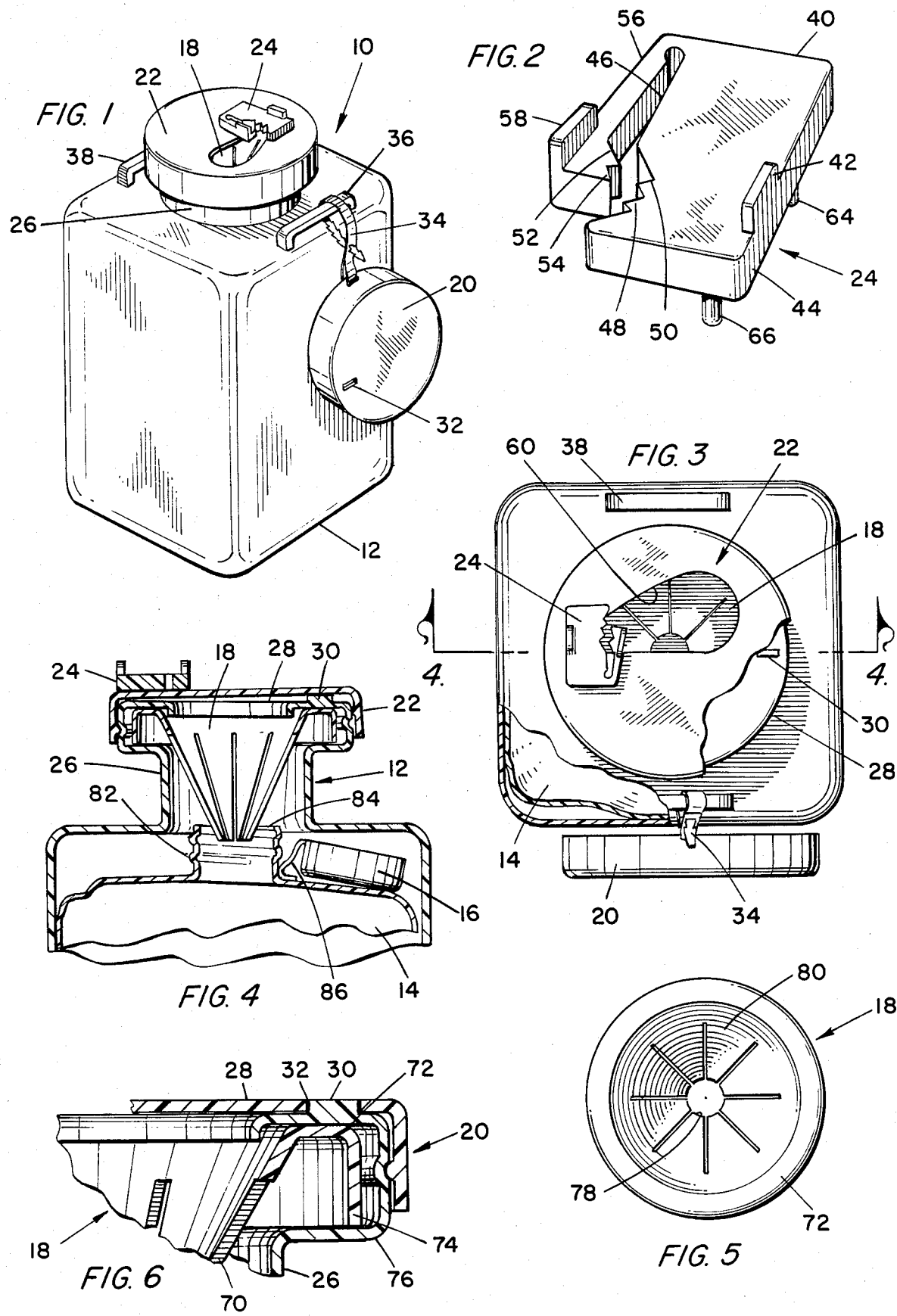

CONTAINER FOR SHARPS

TECHNICAL FIELD

This invention relates to containers for dangerous substances and, in particular, to containers for the containment and destruction or disposition of sharp instruments and harmful substances.

BACKGROUND ART

There is no lack of containers which are capable of receiving and storing a wide variety of dangerous articles and dangerous liquid and fungible materials. As the number and variety suggests, many materials and circumstances require special container designs.

One special circumstance occurs in hospitals, clinics and medical laboratories. In that environment, it is required to dispose of suture needles, razor blades, disposable razors and other cutting implements, syringe needles, and a variety of fungibles (powders and the like) and liquids such as anti-neoplastics. They must be rendered harmless in most cases by incineration or encapsulation in the collapsed container by autoclaving. Because the container is destroyed and often must be destroyed when filled to only a fraction of its capacity, the cost must be minimal.

The logistics problem in hospitals and clinics is immense. In the large, full service, acute hospital, thousands of special purpose items are required to be stocked and dispensed, and those that are required for patient treatment must be give first priority.

In the smaller, specialized medical service units, the amount of facilities and resources devoted to hazardous waste disposal is minimal. The result has been economic pressure for an all purpose disposal system for the waste that is generated during the conduct of medical procedures.

However, the primary demand comes from the physicians and nurses. Experience demonstrates the discipline exhibited by physicians and nurses and aides in the treatment of patients does not extend to disposal of the refuse of the treatment. Unless the means is as available and as easy and convenient as any other means of disposal, the safe, prescribed disposal system will often not be employed. The need is not limited to a disposal system that is effective and safe. Cost and convenience are equally important factors.

The currently available containers are fitted with covers that are slit across the center, most often with two slits at right angles to form four flaps. The cover material is selected to be resilient but stiff enough to retain the flaps in substantially the same plane, whereby the container is substantially completely closed. The flaps are made to yield to permit insertion of articles, but the points of the flaps are made stiff and sharp enough to discourage any attempt, by drug users and the like, to retrieve syringes and syringe needles. The result, however, is that one who attempts to dispose of an article, and must push it through the flaps, risks having his fingers jabbed by the flap points. That is enough to discourage use, and, of course, such a design does not permit safe disposal of liquids.

DISCLOSURE OF INVENTION

An object of the invention is to provide an effective, minimum cost disposal container for dangerous waste material and for the medical service industries in particular.

Another object is to provide a container which is destroyed by incineration and which retains its containment integrity notwithstanding collapse in autoclaving, and which will meet all of the requirements for safe disposal, especially of sharp articles and anti-neoplastic liquids.

A further object is to create such a waste containment and disposal system which is, and which appears to be, safe and convenient and effective to use.

These and other objects and advantages of the invention which will become apparent upon a reading of the description of preferred embodiment, and an examination of the drawings are realized, in part, by the provision of a container system which employs a resilient, conical inner cover which tapers to the interior of the container. The walls are divided into flaps. The preferred embodiment employs a truncated cone whose walls are tapered in thickness and in width toward the apex to make it easily deformable. That facilitates the deposit of articles. If the container is inverted, the flaps overlie one another and tend to complete closure. Further, in the preferred embodiment, the flap cover is not relied on to secure the container shut. It is not necessary to provide security against the container user; he has access to the needles and other articles before they are placed in the container. In the preferred form of the invention the rim of the container is resilient. A keeper, or projection, on the rim is employed as a bolt for disposition in a keeper formed as an opening to receive the bolt in a rigid cover which is fixed to the container. The arrangement can be reversed, of course.

In the preferred embodiment the container is formed with a wide mouthed receiving opening, wide enough to reach in with fingers to seal an inner container which is disposed inside the outer container and which has an upper entry opening accessible through the receiving opening for receiving both solids and liquids as well as for effecting closure. The conical inner falp closure is made easily removable in the preferred embodiment, and is disposable within the container itself.

Alignment of inner and outer containers is facilitated, and removal of material from the container system is aided by the use of a necked container which extends from an upper shoulder of the container and ends in the receiving opening. The inner container is disposed with its opening in the end of the neck and the conical flap closure is arranged so that it terminates near the end of the neck, or somewhat beyond the shoulder of the main body of the container.

Because the locking cover arrangement is effective, and removal of material is far more difficult than in prior designs, there is less reason to hide the fact that a container may contain a syringe or syringe needles. Thus, there is less reason to make the container opaque. In the preferred embodiment the outer container is a translucent red and the inner container is clear or a translucent white.

In certain applications, in the case of the needle disposal container or a blood sample tray, for example, it is desirable to include a means for facilitating the removal and disposition of neeldes from the syringe barrel. A special removable, and reusable, cover for the container is provided as a feature of the invention to accomplish that purpose.

BRIEF DESCRIPTION OF THE DRAWINGS

In the drawings:

FIG. 1 is an isometric view of a preferred form of a dangerous material disposal system according to the invention;

FIG. 2 is an isometric view of the needle removal structure of FIG. 1 as it appears before assembly with the cover;

FIG. 3 is a fragmented, partly sectioned top plan view of the structure of FIG. 1;

FIG. 4 is a fragmented, cross-sectional view taken on line 4—4 of FIG. 3;

FIG. 5 is an enlarged cross-sectional view of the upper right portion of FIG. 4 except that one cover has been exchanged for another; and FIG. 6 is a top plan view of the conical closure element of the assembly of FIG. 1.

DESCRIPTION OF THE PREFERRED EMBODIMENT

The preferred form of the invention is illustrated in FIG. 1 of the drawing. What is shown is a system which is generally designated 10. It includes an outer container 12. Except that the preferred form has a mouth wide enough to permit one to reach through the container neck, down into the upper portion of the body of the container, size is not a feature of the invention. Other container shapes and sizes relative to the cover are envisioned within the invention.

The complete system 10, in addition to the wide mouth necked outer container 12 includes an inner container 14 portions of which are visible in FIGS. 3 and 4. It also includes a closure member which, in this case, is a cover 16 for the inner container, and it includes a tapered closure member 18 which is disposed with its rim portion adjacent to the rim of the receiving opening of the outer container and is tapered inwardly to the interior of the container. That element is shown in top plan view in FIG. 5, and it is visible in FIGS. 1, 3, 4 and 6.

The system includes two covers which may be fixed to the outer container to overlie its receiving opening. One of those covers is numbered 20 in FIGS. 1 and 3, and its function is to lock the container against reopening and reentry when access to the interior is no longer required. The cover 22, which is shown to be fitted on the container in FIGS. 1, 3, 4 and 6, is fitted with a structure which facilitates removal of syringe needles from the syringe barrel. That structure is numbered 24 in the drawings. It is shown in FIG. 2, and is visible in FIGS. 1, 3 and 4. Thus it is that the system includes an outer container, a tapered inner closure member for the outer container, and two covers for the outer container, and an inner container, and a closure cover for the inner container.

In the preferred form of the invention the cover for the inner container is fixed to the inner container. The inner container is resilient, and even pliant, so that it may be readily removed from the outer container. The outer container is resilient and sufficiently rigid to retain its shape and form in the absence of the application of a substantial amount of pressure.

The tapered closure 18 is made of a resilient material and is also removable in the event that removal is required in a particular circumstance.

In the preferred form the inner container is transparent or translucent. When combined with a translucent outer container it is possible to determine from the exterior of the unit the degree in which the containers are filled.

In preferred form the several elements which comprise the system are formed of material which will incinerate without emission of harmful or toxic fumes. Polyethylene plastic is suitable, and is now preferred.

In this embodiment the container 12 is approximately square with rounded corners in horizontal cross-section at a point below the neck region 26 if the cover 22 is considered to be at the upper side of the container. In a typical case, the cover itself would be about four inches in diameter. The neck of the container would be about three inches in diameter, and the container width and breadth about six inches. In this case the neck 26 is about one inch long, and it widens to almost four inches in diameter at its upper end in the region of the rim 28.

There is a projection 30 at the upper edge of the rim. That projection is best seen in FIG. 3 and in the enlargement of FIG. 6 where it is shown to be relatively narrow and to extend radially and upwardly from the rim 28.

The wall of the outer container 12 is relatively thin, and its design is such as to permit it to be manufactured by the blow mold process. That process permits formation of threads on the exterior surface of the neck just below the rim to accommodate mating threads of the cover 22. In the preferred embodiment the cover is made of relatively rigid material. When it is screwed on to the outer container it bears against the projection 30. However, the rim 28 is formed of a material that yields and deforms sufficiently to permit the cover 20 to be screwed into place.

The locking cover 20 is shown in FIG. 1 to be formed with a slot 32 at one point around its upper margin. That slot has size to accommodate the projection 30. The cover 20 is made of a relatively rigid material. When it is screwed on to the upper end of neck 26, the rim of the container and the projection 30 are deformed and forced downwardly until, finally, when the cover 20 is screwed on fully, or nearly so, the slot 32 is turned to a position over the projection 30. The resilience of the rim 28 then forces the projection 30 upwardly into the slot 32. The projection 30 then operates as a deadbolt in cooperation with the keeper formed by slot 32, and further rotation of the cover 20 relatively to the container 12 is precluded. The keeper is shown lodged in the slot 32 in FIG. 6.

The cover 20 is secured by an integrally formed tie filament 34 to handle 36 which is one of two handles integrally formed with the upper surface of the body of outer container 12. The other handle is visible in FIGS. 1 and 3 where it is numbered 38. The arrangement shown is preferred. Hospital personnel customarily carry scissors by which the tie is easily cut. It is cut and the cover 20 is used only when it is desired to seal the container closed preparatory to its ultimate disposition.

When the system is in use, prior to final closure, the cover 22 is left on the outer container 12 ready for the system's most frequent use as a repository for syringes and syringe needles. Cover 22 is provided with an elongated, generally oval shaped opening which extends through the cover and is sufficiently large to receive a disposable razor blade with its holder and handle and the whole of a syring and other small objects.

At one end of the opening a means is provided for permitting convenient removal of syringe needles from the syringe barrel. The preferred structural arrangement is shown in the drawings. As best shown in FIG. 2 the unit includes a generally rectangular base 40 which has uniform thickness except for a finger panel 42 which extends upwardly from the rearward edge 44 of the device. At its forward edge 46 the structure is cut away to form a series of teeth in the edge wall opposite the thumb panel 42. Two teeth are shown in this embodiment and they are designated 48 and 50, respectively. Those teeth cooperate with the teeth 52 and 54 which are formed at the end of a lever 56 at that side of the lever which faces the teeth 48 and 50. At the other side of the lever it is integrally formed with a second thumb panel 58. In preferred form the entire unit is molded of a resilient plastic. The lever 56 is molded so that it stands away from the base section 40 in relaxed condition. In that condition the nut by which the needle is fastened to the barrel in a conventional syringe is easily inserted between the two sets of teeth. By squeezing the lever to the base by pressure applied at the two finger panels 42 and 58, the fastening element of the needle is prevented from rotation. In that circumstance the barrel is easily twisted off of the needle either to be saved or to be deposited separately in the elongated opening 60 of the cover. When pressure on the panels 42 and 50 is released the needle, a portion of which already extends down through opening 60, is released to fall through the opening into the interior of the container.

The two sections of the clamping structure, i.e. the lever and the base, can be considered to be a pair of jaws which are manually operable to clamp down on the fastening element of the syringe needle. The clamping structure is secured to the cover 22 by a plurality of integrally formed projections which extend down through perforations in the cover and are there thermally upset so that they serve as rivets. Two of those projections are visible in FIG. 2 where they are numbered 64 and 66, respectively.

Cover 22, with its needle removing clamping jaws, is especially useful in the circumstance in which a number of syringes are to be used within a relatively short space of time. It is useful whether or not the syringe barrel is to be reused. Good practice, indeed, the required practice in many jurisdictions, is that the needle be removed prior to disposal of the syringe so that the clamping jaws are useful even when the entire syringe is to be disposed. Furthermore, in some cases the requirement is that the needle be broken prior to disposal. The jaws of the clamping unit here shown are arranged so that the thin needle can be pinched between them and broken off by twisting of the barrel and needle shank. In that case, if the barrel is to be reused, the clamp is simply used again to remove the needle fastening element.

Whether the cover 22 is used or not, there is a need to prevent materials already contained within the unit from being removed. To that end the invention provides the function performed by the prior art flap covers but in a form that avoids the disadvantage of the prior art structures. The closure element 18 extends across the mouth of the container. Its outer margin is formed with a flange which fits and is trapped in place below the rim in the outer portion of the container neck. In this preferred embodiment the member 18 has an outwardly extending flange which turns down into an integrally formed cylindrical wall. The closure member is formed of a resilient material that is readily deformable in a way that permits insertion of the element into the neck. When pressure is relaxed the flange springs outwardly and is trapped in the enlarged proportion of the container neck.

The central region of the closure member, instead of lying flat as in the prior art, is tapered inwardly. The preferred form is conical as shown. It could be tapered to an apex, but in the preferred form the inner end is truncated in small degree to provide an opening through which insertions are easily and readily made. The side walls of the conical insert are slit, in this case by eight radial slits evenly spaced around the side wall of the cone. They divide the cone wall into eight flaps. The cone material is resilient and, in preferred form, is just stiff enough to preserve the conical shape, but the flaps yield easily and, to facilitate that, the thickness of the cone wall is reduced in the direction of the taper. That feature is particularly visible in FIG. 6 where the section through the conical member 18 is taken parallel to one of the slits to expose the side wall 70 of the slit. It can be seen to taper to smaller thickness in the direction of the apex of the structure. For identification the flange of the conical closure member is identified by the reference numeral 72 in FIG. 6 where it is shown turned down to form a cylindrical outer wall 74. The wall 74 and the flange 72 are trapped in the enlarged portion 76 of the neck 26. If the container is inverted and an article is made to fall down upon that conical member, its weight will tend to force the several flaps of the closure member to overlap and to close the central opening which occurs where the cone is truncated. The effect is to prevent those articles from falling from the container. Needles and other small metallic sharps are especially mobile and tend to fall as the container is inverted along the side walls and down into the region adjacent to the flange 72 and the peripheral wall 74. Thus it is that notwithstanding that the conical member is truncated, small sharps are retained even more effectively than in the older designs in which the relatively rigid flaps of the closure member tend to lie in a common plane.

The conical structure is shown in top plan view in FIG. 5 where the central opening is designated 78, and one of the flaps is designated 80 for identification.

The preferred embodiment includes an inner container 14 which is relatively more pliant than the outer container 12. It is provided with a neck 82 which opens at its upper end in an upper opening 84. The neck 82 is threaded to receive cooperating threads formed internally in the cover 16. In this embodiment the cover is fixed, as by sonic bonding or any other convenient means, to the exterior wall of the container wall 14. The tie 86 is integrally formed with the cover and is bonded sonically to the container. That interconnection is sufficiently strong so that the cover will be removed with the container if removal is desired. It is necessary only to reach in and grasp one or two flaps of the closure member 18 and to pull it from its trapped position under the rim 28 to afford access to the inner container. The neck of the inner container is arranged substantially centrally along the axis of the neck 26 and is readily accessible. One need only reach in and grasp the neck and pull the inner container out if, for any reason, that is desired. Similarly, when the inner container is to be filled with liquid, it is a simple matter to remove the closure element 18, to drain the liquid to be disposed of down through the neck 26 into the container 14, and then to reach in and grasp the cover 16 and to screw it on to the top of the inner container. If the member 18 is to be disposed of it is reinserted into the neck to the position shown in FIG. 4 or to the interior of the container if the inner container is pushed outwardly and the unit is sealed by screwing on the cover 20 until the projection 30 locks into the slot 32.

In regular usage the conical closure element 18 and the inner container 14 are assembled in the fashion shown in FIg. 4. That is true whether the cover 22 is assembled on the container or not. Sharps entering the cone simply fall down into the inner container, and that is preferred because, in that circumstance, there are two container walls to perform the confining function. In the event that a larger syringe, too large to enter the neck of the container, is inserted into the unit, the inner container is simply forced down to accommodate the larger object.

Not only will this disposal system serve as effectively, and ordinarily more effectively, in the containment and disposal of dangerous material that has been true of prior art designs, but the system has the very substantial advantage that it will serve as an easily used and convenient recepticle for dangerous material in a wide range of the circumstances in which the waste from medical procedures is generated in the hospital and clinic environment.

Although we have shown and described certain specific embodiments of our invention, we are fully aware that many modifications thereof are possible. Our invention, therefore, is not to be restricted except insofar as is necessitated by the prior art.

We claim:

1. A disposal system for dangerous materials comprising in combination:
    a container having a receiving opening and defining a support portion,
    a thin walled closure element having a first portion supported by the support portion of the container and having a second portion extending into the container through the receiving opening, the second portion of said closure element being cut to form at least a pair of resilient inner flaps, and
    a cover supported on the container for closing the receiving opening,
    the container and the cover having detents engageable with each other to retain the cover in locked relationship on the container.

2. A system as defined in claim 1 wherein the second portion of said closure element has the shape of an inverted truncated cone.

3. A system as defined in claim 2 wherein the second portion of the closure element is formed with a plurality of flaps extending radially from the truncated end for a distance less than the length of the closure member and wherein the flaps extend through the thickness of the closure element.

4. A system as defined in claim 3 wherein the thickness of said second portion of said closure element is tapered in the direction of its truncated end.

5. A system as defined in claim 1, wherein means are provided in the form of interfitting threads on the cover and the container and wherein an opening is provided in one of the cover and the container and a projection is provided on the other one of the cover and the container to lodge in said opening upon interfitting of the threads of the cover and the container.

6. A system as defined in claim 1 wherein the dangerous materials include a syringe having a needle and wherein the cover for the receiving opening of said container is formed with a through entry opening and clamping means are disposed on the cover and are associated with said through entry opening for clamping the needle of the syringe against rotation with the barrel of the syringe to provide for a removal of the needle from the syringe and a disposal of the needle in the container through the through entry opening.

7. A system as defined in claim 6 wherein said clamping means includes a base fixed to said cover adjacent to said through entry opening and further includes a clamping lever pivotally carried by said base.

8. A system as defined in claim 7 wherein said base and said lever form jaws resiliently biased for disposition in a spaced relationship and responsive to manual pressure to close and wherein the needle is adapted to be disposed in the spaced relationship between the jaws.

9. A system as defined in claim 1 wherein an inner container is disposed within the first container and is provided with an upper opening to receive the dangerous objects passed through said receiving opening in the first container; and wherein
    a closure member is operably coupled to the inner container to close said upper opening in the inner container.

10. A system as defined in claim 1 wherein said container is formed with a neck and an enlarged portion at the upper end of the neck and wherein said receiving opening is formed in said neck and in the enlarged portion at the upper end of the neck and wherein the flaps in said closure element extend through substantially the entire heighth of said neck.

11. A system as defined in claim 1 in which the second portion of said closure element is conical and is tapered at not less than twenty-five degrees from the central longitudinal axis of the closure element to define the conical configuration.

12. In a system for disposing of dangerous materials including a syringe having a needle portion:
    a hollow container,
    a cover for the container, the cover being formed with a through entry opening; and
    needle removal means in the form of a pair of jaws mounted on said cover and pivotable relative to each other for grasping the needle portion of the syringe when the needle portion of the syringe extends into said through entry opening.

13. A system as defined in claim 12 wherein one jaw of said pair of jaws is fixed and the other jaw of said pair is resiliently mounted on the closure cover for clamping and unclamping movement pivotally toward and away from said one jaw.

14. A system as defined in claim 13 wherein said other jaw is normally biased away from said one jaw.

15. A system as defined in claim 12, including, the container having a receiving opening, said cover and said container being formed with interfitting means for securing the cover to said container over said receiving opening.

16. A system as defined in claim 15 wherein said container has an upper rim formed of resilient material and wherein said rim encompasses said receiving opening and is formed with a projection extending in a direction away from the interior of the container and wherein
    the cover has an opening to receive said projection upon being secured to the container.

17. In a disposal system:
    a substantially rigid outer container having a receiving opening;

a substantially pliant inner container disposed within said outer container and having an upper opening accessible through said receiving opening;

inner container closure means disposed in said outer container and operably coupled to the inner container for closing the upper opening of the inner container;

outer container closure means carried by said outer container and operably coupled to the outer container for closing the outer container; and means disposed in cooperative relationship on the outer container and the outer container closure means effective upon closing the outer container to prevent its being reopened.

18. A system as defined in claim 17 wherein the rim of said receiving opening in the outer container is resilient and is formed with a projection extending from said rim andwherein said outer container closure means includes a cover and an opening in the cover to receive said projection and wherein cooperating conformations are provided on the outer container and the outer container closure means to interlock the conformations.

19. A system as defined in claim 17 wherein said outer container is formed with a neck having said receiving opening formed at the upper end of the neck and wherein the upper opening of the inner container is disposed in alignment with said receiving opening within the inner end of said neck.

20. In combination for disposing of dangerous medical objects, a hollow container having a neck portion and having an opening in the neck portion for receiving the dangerous objects, the container having an enlarged portion extending upwardly from the neck portion and having an opening communicating with the opening in the neck portion, a closure element having a first portion supported by the enlarged portion of the container and having a second portion extending downwardly into the opening in the neck portion in a direction progressively restricting the dimensions in the opening in the neck portion, the second portion of the closure element being slit to define flaps, and a cover disposed on the container for an interlocked relationship with the enlarged portion of the container and constructed to cover the closure element in such interlocked relationship.

21. A combination as set forth in claim 20 wherein the height of the enlarged portion of the hollow container is defined by oppositely disposed walls and wherein the first portion of the closure member is supported between such oppositely disposed walls.

22. A combination as set forth in claim 20 wherein the first portion of the closure element is supported within the enlarged portion of the container.

23. A combination as set forth in claim 20 wherein the second portion of the closure element is tapered as it extends downwardly.

24. A combination as set forth in claim 21 wherein the second portion of the closure element is tapered as it extends downwardly and wherein means are provided on the enlarged portion of the container and on the cover to define the interlocked relationship.

25. A combination as set forth in claim 20 wherein the dangerous medical objects include a syringe having a needle and wherein means are provided on the cover to define a nutcracker relationship operable to grasp the needle for separation of the needle from the syringe and wherein the cover is provided with an opening at the nutcracker arrangement to provide for a movement of the needle into the container when the needle is separated from the syringe and the nutcracker relationship is released.

26. A combination as set forth in claim 20 wherein the enlarged portion and the neck portion of the container define a pair of spaced walls in the container and wherein the first portion of the closure element is confined between the pair of spaced walls defined by the enlarged portion and the neck portion of the container.

27. In combination for disposing of dangerous objects, a hollow container having a hollow neck portion extending upwardly from the container and defining an opening at the upper end of the neck portion, a closure element having a first portion supported by the neck portion, the closure element also having a second portion extending downwardly into the neck portion in a frusto-conical configuration, the second portion being slit to define flaps, the closure element being made from a resilient material to provide for the pivotal movement of the flaps downwardly upon an insertion of the dangerous objects into the container and to provide for a return of the flaps to their original positions after such insertion, and a cover disposed on the container for covering the opening in the container in an interlocked relationship with the container.

28. A combination as set forth in claim 27 wherein the dangerous objects include syringes having needles and wherein means are disposed on the cover for releasably grasping the needles to facilitate removal of the needles from the syringes and wherein an opening is provided in the cover at the position of the grasping means to provide for the disposition of the needles in the container after removal of the needles from the syringes.

29. A combination as set forth in claim 27 wherein the thickness of the second portion of the closure element is tapered as such second portion extends downwardly into the neck portion of the container.

30. A combination as set forth in claim 27 wherein the first portion of the closure element is supported by the container within the neck portion of the container and wherein the second portion of the closure element is constructed to pass the dangerous objects into the container but to resist the passage of the dangerous objects from the containers.

31. A combination as set forth in claim 30 wherein the thickness of the second portion of the closure element is tapered as the second portion extends downwardly into the neck portion of the container and wherein the dangerous objects include syringes having needles and wherein means are disposed on the cover for releasably grasping the needles to facilitate removal of the needles from the syringes and wherein an opening is provided in the cover at the position of the grasping means to provide for the disposition of the needles in the container after the removal of the needles from the syringes.

32. In combination for disposing of dangerous objects, a closure element made from a resilient material and having a first portion outwardly disposed and shaped to provide a retaining function, the closure element having a second portion integral with the first portion and extending in a frusto-conical path from the first portion and defining an opening in the frustum of the cone, the second portion being slitted in the second portion to define at least a pair of flaps constructed to pass the dangerous objects in the direction of the decreasing opening in the cone but to oppose the passage of the dangerous objects in the opposite direction through the cones, a hollow container having a neck portion at its upper end, the neck portion defining an opening for receiving the dangerous objects and for passing the dangerous objects into the hollow container, the neck portion of the hollow container being shaped to retain the first portion of the closure element in fixed position and to provide for an extension of the second portion of the closure element into the neck portion, and a cover operatively coupled to the container to fit over the neck portion of the container in interlocking relationship with the container.

33. A combination as set forth in claim 32 wherein the first portion of the closure element is retained within the neck portion of the container and wherein the cover and the container are provided with complementary portions for defining cooperating detents to maintain the cover and the container in interlocking relationship.

34. A combination as set forth in claim 32 wherein the neck portion of the container has a pair of spaced walls and wherein the first portion of the closure member is confined between the spaced walls on the neck portion of the container.

35. A combination as set forth in claim 32 wherein the neck portion of the container has an enlarged portion at its upper end and the enlarged portion has an opening for passing the dangerous objects into the container and wherein the heighth of the enlarged portion is defined by a pair of spaced walls and wherein the first portion of the closure member is retained in fixed position between the pair of spaced walls in the enlarged portion of the container.

* * * * *